United States Patent
Kopacki et al.

(10) Patent No.: US 10,143,694 B2
(45) Date of Patent: Dec. 4, 2018

(54) ADVANCED FORMULATIONS AND THERAPIES FOR TREATING HARD-TO-HEAL WOUNDS

(71) Applicants: Matthew H. Kopacki, Ringwood, NJ (US); Michael J. Torsiello, Oakland, NJ (US)

(72) Inventors: Matthew H. Kopacki, Ringwood, NJ (US); Michael J. Torsiello, Oakland, NJ (US)

( * ) Notice: Subject to any disclaimer, the term of this patent is extended or adjusted under 35 U.S.C. 154(b) by 0 days.

(21) Appl. No.: 14/462,894

(22) Filed: Aug. 19, 2014

(65) Prior Publication Data

US 2014/0357645 A1    Dec. 4, 2014

Related U.S. Application Data

(63) Continuation-in-part of application No. 12/380,128, filed on Feb. 24, 2009, now abandoned, which is a continuation-in-part of application No. 11/978,293, filed on Oct. 29, 2007, now abandoned, application No. 14/462,894, filed on Aug. 19, 2014, which is a continuation-in-part of application No. 12/380,102, filed on Feb. 24, 2009, now abandoned, which is a continuation-in-part of application No. 11/978,293, filed on Oct. 29, 2007, now abandoned, application No. 14/462,894, filed on Aug. 19, 2014, which is a continuation-in-part of application No. 12/380,127, filed on Feb. 24, 2009, now abandoned, which is a continuation-in-part of application No. 11/978,293, filed on Oct. 29, 2007, now abandoned.

(60) Provisional application No. 60/854,805, filed on Oct. 27, 2006.

(51) Int. Cl.

| | |
|---|---|
| *A61K 31/522* | (2006.01) |
| *A61K 31/44* | (2006.01) |
| *A61K 31/4418* | (2006.01) |
| *A61K 31/506* | (2006.01) |
| *A61K 31/517* | (2006.01) |
| *A61K 31/52* | (2006.01) |
| *A61K 45/06* | (2006.01) |
| *A61K 9/00* | (2006.01) |
| *A61K 9/06* | (2006.01) |
| *A61K 47/24* | (2006.01) |

(52) U.S. Cl.
CPC ............ *A61K 31/522* (2013.01); *A61K 31/44* (2013.01); *A61K 31/4418* (2013.01); *A61K 31/506* (2013.01); *A61K 31/517* (2013.01); *A61K 31/52* (2013.01); *A61K 45/06* (2013.01); *A61K 9/0014* (2013.01); *A61K 9/06* (2013.01); *A61K 47/24* (2013.01)

(58) Field of Classification Search
CPC .................................................. A61K 31/522
See application file for complete search history.

(56) References Cited

U.S. PATENT DOCUMENTS

| | | |
|---|---|---|
| 4,912,111 A | 3/1990 | Sank et al. |
| 6,117,877 A | 9/2000 | Fogel |
| 2002/0065286 A1 | 5/2002 | Davies et al. |
| 2002/0160995 A1* | 10/2002 | Easterling ................ 514/211.07 |
| 2003/0176442 A1 | 9/2003 | Wood et al. |
| 2005/0008592 A1* | 1/2005 | Gardel ..................... A61K 8/06 424/63 |
| 2005/0181028 A1* | 8/2005 | Foote et al. .................. 424/445 |

FOREIGN PATENT DOCUMENTS

| | | | |
|---|---|---|---|
| WO | WO 2004024180 A1 * | 3/2004 | |
| WO | WO 2005/070433 A1 | 8/2005 | |

OTHER PUBLICATIONS

Spentzouris et al., The Evaluation of Lower-Extremity Ulcers, 2009, Seminars in Interventional Radiology, vol. 26, No. 4, pp. 286-295.*
Transdermal Nifedipine for Would Healing: Case Reports, International Journal of Pharmaceutical Compounding, vol. 4, No. 5, Sep./Oct. 2000, pp. 356-358.
Godwin et al., Influence of Transcutol CG on the skin accumulation and transdermal permeation of ultraviolet absorbers, 2002, European Journal of Pharmaceutics and Biopharmaceutics, 53, pp. 23-27.
Murdan, S., A review of pluronic lecithin organogel as a topical and transdermal drug delivery system, 2005, Hospital Pharmacist, vol. 12, pp. 267-270.
TheFreeDictionary.com reference [Retrieved on Mar. 14, 2011 from the Internet: <URL: http://www.thefreedictionary.com/wound].
Courtney et al. (Metabolism, vol. 52, No. 9, pp. 1147-1152; Sep. 2003.

(Continued)

*Primary Examiner* — Kortney L. Klinkel
*Assistant Examiner* — Tori Strong
(74) *Attorney, Agent, or Firm* — King & Partners, PLC

(57) ABSTRACT

A method for healing a hard-to-heal wound including the steps of: topically administering a wound healing composition to a wounded area, wherein the wound healing composition includes, at least one of: (a) a medicament characterized as a calcium channel blocker or pharmaceutically acceptable salts or solvates thereof; (b) a medicament characterized as an alpha-adrenergic antagonist or pharmaceutically acceptable salts or solvates thereof; (c) a medicament characterized as a direct vasodilator or pharmaceutically acceptable salts or solvates thereof; and (d) a medicament characterized as a phosphodiesterase type five inhibitor or pharmaceutically acceptable salts or solvates thereof; and (e) a hemorrheologic agent or pharmaceutically acceptable salts or solvates thereof; (f) a primary dermal penetrating agent or pharmaceutically acceptable salts or solvates thereof: and (g) a topical stimulating agent or pharmaceutically acceptable salts or solvates thereof.

2 Claims, 8 Drawing Sheets

(56) References Cited

OTHER PUBLICATIONS

Cleland (Cardiovascular Drugs and Therapy, vol. 11, pp. 297-303; 1997.
Vinik et al. (Clinical Diabetes, vol. 14, No. 5, Sep./Oct. 1996).
Chen et al. (Am J Physiol Heart Circ Physiol, vol. 284, pp. 1513-1520; 2003).

* cited by examiner

ADVANCED FORMULATIONS AND THERAPIES FOR TREATING HARD-TO-HEAL WOUNDS

CROSS REFERENCE TO RELATED APPLICATIONS

This application is a continuation-in-part of U.S. application Ser. No. 12/380,128, filed Feb. 24, 2009, entitled "METHOD FOR HEALING A WOUND USING AN ALPHA-ADRENERGIC ANTAGONIST," and U.S. application Ser. No. 12/380,102, filed Feb. 24, 2009, entitled "METHOD FOR HEALING A WOUND USING A DIRECT VASODILATOR," and U.S. application Ser. No. 12/380,127, filed Feb. 24, 2009, entitled "METHOD FOR HEALING A WOUND USING A PHOSPHODIESTERASE TYPE FIVE INHIBITOR," all of which are continuations-in-part of U.S. application Ser. No. 11/978,293, filed Oct. 29, 2007, entitled "METHOD FOR HEALING A WOUND," which claims the benefit of U.S. Provisional Application Ser. No. 60/854,805, filed Oct. 27, 2006, entitled "METHOD FOR HEALING A WOUND," all of which are hereby incorporated herein by reference in their entirety—including all references cited therein.

BACKGROUND OF THE INVENTION

1. Field of the Invention

The present invention relates in general to advanced formulations and therapies for treating hard-to-heal wounds and, more particularly, to therapies for treating hard-to-heal wounds via localized application of novel and advanced topical formulations. Notably, these advanced formulations and therapies have unexpectedly proven to be remarkably successful in last resort situations. For example, when conventional therapies have failed and the patient is imminently susceptible and/or vulnerable to, for example, amputation of an extremity and/or death.

2. Background Art

In today's society, many people suffer from hard-to-heal wounds that are refractory to conventional forms of treatment. Such hard-to-heal wounds may include wounds of diabetic origin, diabetic skin sores, pressure sores, vessel disease wounds, surgery wound breakdown, spinal injury wounds, and chemical wounds—just to name a few.

To be sure, the human body's healing process is very complex and requires several steps. According to The Wound Care Information Center, sponsored by the Wound Care Center at Presbyterian Hospital of Dallas, normal healing requires that cells proliferate and divide, thereby releasing growth factors. In turn, new blood vessels are produced, a collagen matrix is formed, and remodeling occurs. Each step requires appropriate substrates and nutritional elements to be present and available. However, for some patients, certain conditions alter this course, thereby disrupting the healing process. In such cases, the wound can become chronic. In America alone, approximately five million (5,000,000) people are battling chronic open sores which may become seriously infected, gangrenous, and may eventually require amputation.

In addition, the Wound Care Information Center estimates that there are approximately sixteen million (16,000,000) diabetics in America. Diabetes causes microangiopathic changes in, among other places, the foot, which is a common site for non-healing wounds. It is not uncommon for diabetic patients to have to undergo surgical amputation as a result of a non-healing wound and must then face a lifetime of costly rehabilitation, and permanently reduced mobility and independence.

Other conditions which can lead to the development of non-healing wounds include peripheral vascular disease, arterial or venous ulcers, traumatic injury, complications following surgery, rheumatoid arthritis, congestive heart failure, lymphedema, and other conditions which compromise circulation. In addition, local factors such as pressure, infection, or edema, and systemic problems which leave patients immunocompromised, such as collagen vascular disease, acquired immunodeficiency syndrome, rheumatoid arthritis, or diabetes mellitus, can impair normal healing. Furthermore, some medications can suppress the body's healing process and inadequate large-vessel perfusion and oxygenation impedes healing by reducing the oxygen supply to the damaged tissue.

At this time, wound treatment programs and intervention include conventional and advanced wound dressings, removal of unhealthy tissue, bioengineered tissue, hyperbaric (high-pressure) oxygen treatment, growth factors (isolated, concentrated substances that are applied topically to the wound to stimulate healing), antibiotic therapy, nutrition counseling, education and prevention, surgery, physical therapy, and protective footwear, among others.

Patients suffering from such wounds and/or chronic open sores typically seek specialized professional help after their wounds have not healed during months of standard wound treatment. However, even the most advanced methods for healing wounds can take several additional months and are not always successful.

Therefore a need of the present invention exists to provide advanced formulations and therapies for treating hard-to-heal wounds via localized application of both novel and advanced topical formulations, especially in last resort situations when conventional therapies have failed and the patient is imminently susceptible and/or vulnerable to amputation of an extremity and/or death.

These and other needs of the present invention will become apparent in light of the present specification, claims, and drawings.

SUMMARY OF THE INVENTION

The present invention is directed to, in one embodiment, a method for healing a wound, consisting of, consisting essentially of, and/or comprising the steps of: topically administering a wound healing composition to a wounded area, wherein the wound healing composition comprises: a medicament characterized as a calcium channel blocker or pharmaceutically acceptable salts or solvates thereof; a medicament characterized as a hemorrheologic agent or pharmaceutically acceptable salts or solvates thereof; a dermal penetrating agent or pharmaceutically acceptable salts or solvates thereof; and a topical stimulating agent or pharmaceutically acceptable salts or solvates thereof.

In a preferred embodiment of the present invention, the step of topically administering a wound healing composition comprises the step of topically administering a wound healing composition which comprises a medicament represented by the following chemical structure:

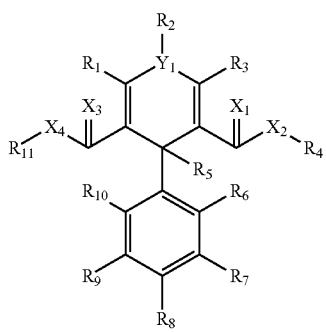

wherein $R_{1-11}$ are the same or different and comprise H, a hydroxy group, a primary, secondary, or tertiary amine, a halide, $NO_2$, $SO_3H$, CN, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof, wherein $X_{1-4}$ are the same or different and comprise oxygen, sulfur, or selenium; and wherein $Y_1$ comprises nitrogen or phosphorus.

In another preferred embodiment of the present invention, the step of topically administering a wound healing composition comprises the step of topically administering a wound healing composition which comprises a medicament represented by the following chemical structure:

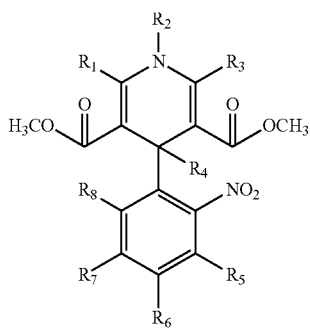

wherein $R_{1-8}$ are the same or different and comprise H, a hydroxy group, a primary, secondary, or tertiary amine, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof.

In yet another preferred embodiment of the present invention, the step of topically administering a wound healing composition comprises the step of topically administering a wound healing composition which comprises a medicament represented by the following chemical structure:

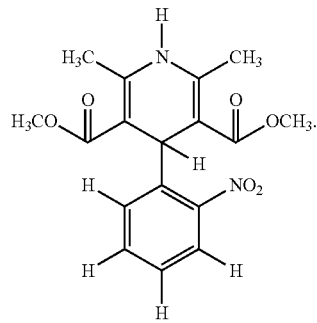 [SMILES: COC(=O)C1=C(C)NC(C)=C(C(=O)OC)C1c1ccccc1[N+](=O)[O-]]

In another aspect of the present invention, the step of topically administering a wound healing composition comprises the step of topically administering a wound healing composition which comprises a medicament represented by the following chemical structure:

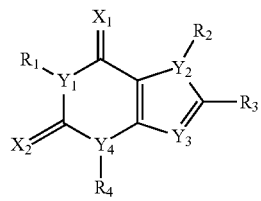

wherein $R_{1-4}$ are the same or different and comprise H, a hydroxy group, a primary, secondary, or tertiary amine, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof; wherein $X_{1-2}$ are the same or different and comprise oxygen, sulfur, or selenium; and wherein $Y_{1-4}$ are the same or different and comprise nitrogen or phosphorus.

In a preferred embodiment of the present invention, the step of topically administering a wound healing composition comprises the step of topically administering a wound healing composition which comprises a medicament represented by the following chemical structure:

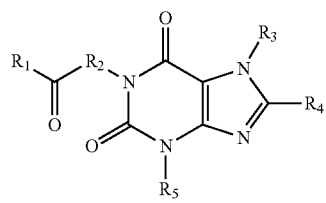

wherein $R_{1-5}$ are the same or different and comprise H, a hydroxy group, a primary, secondary, or tertiary amine, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof.

In another preferred embodiment of the present invention, the step of topically administering a wound healing composition comprises the step of topically administering a wound healing composition which comprises a medicament represented by the following chemical structure:

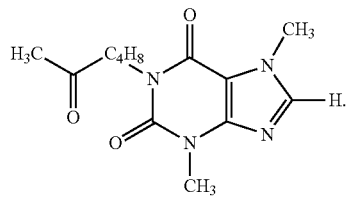

In a preferred embodiment of the present invention, the step of topically administering a wound healing composition comprises the step of topically administering a wound healing composition which comprises a dermal penetrating agent represented by the following chemical structure:

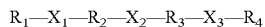

wherein $R_{1-4}$ are the same or different and comprise H, a hydroxy group, a primary, secondary, or tertiary amine, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof; and wherein $X_{1-3}$ are the same or different and comprise oxygen, sulfur, or selenium.

The present invention is also directed to, in one embodiment, a method for healing a hard-to-heal wound of diabetic origin otherwise subject to amputation, comprising the steps of: topically administering a wound healing composition only to the outer periphery of the wounded area of diabetic origin, wherein the wound healing composition comprises at least one of: (a) a medicament characterized as a calcium channel blocker or pharmaceutically acceptable salts or solvates thereof; (b) a medicament characterized as an alpha-adrenergic antagonist or pharmaceutically acceptable salts or solvates thereof; (c) a medicament characterized as a direct vasodilator or pharmaceutically acceptable salts or solvates thereof; and (d) a medicament characterized as a phosphodiesterase type five inhibitor or pharmaceutically acceptable salts or solvates thereof; and (e) a hemorrheologic agent or pharmaceutically acceptable salts or solvates thereof; (f) a primary dermal penetrating agent or pharmaceutically acceptable salts or solvates thereof: and (g) a topical stimulating agent or pharmaceutically acceptable salts or solvates thereof.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted. It will be understood that the invention is not necessarily limited to the particular embodiments illustrated herein.

The invention will now be described with reference to the drawings wherein.

DETAILED DESCRIPTION OF THE INVENTION

Figure 1:
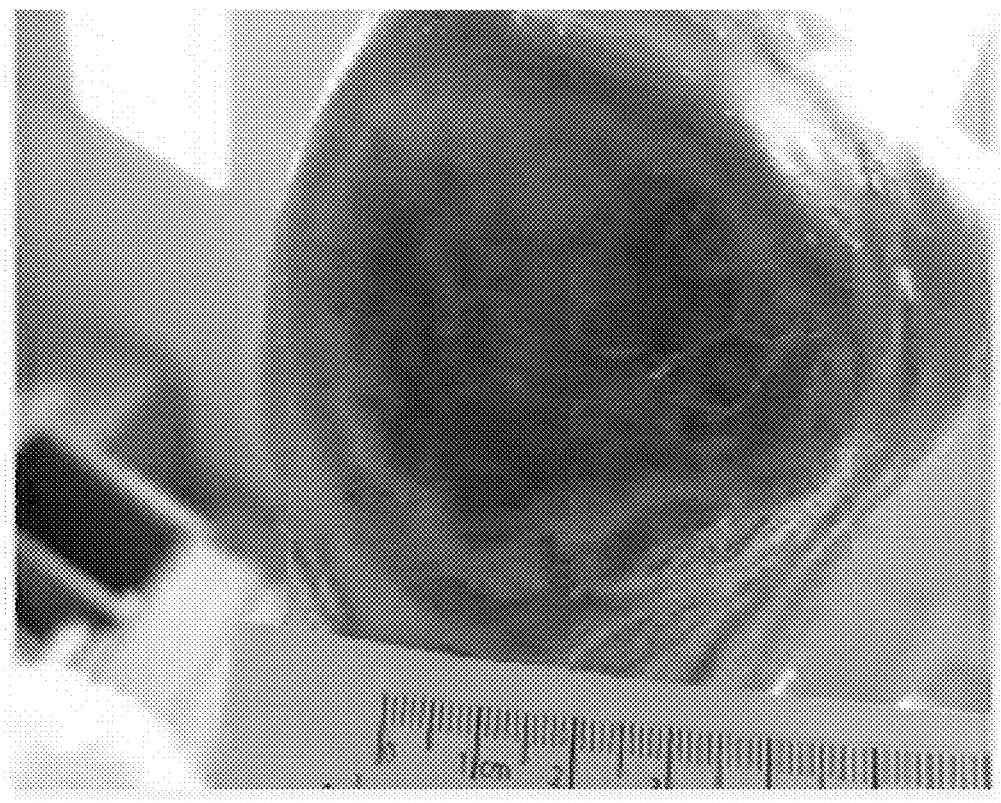
FIG. 1 of the drawings is a pre-therapy photograph of a wound of patient one.

While this invention is susceptible of embodiment in many different forms, there is shown in the drawings and will be described herein in detail, one or more specific embodiments with the understanding that the present disclosure is to be considered as an exemplification of the principles of the invention and is not intended to limit the invention to the embodiments illustrated.

In accordance with the present invention, advanced formulations and therapies for treating wounds, including, but not limited to, hard-to-heal wounds of diabetic origin otherwise subject to amputation, are disclosed.

Wound Characterization:

According to woundcarecenters.org, a wound is typically classified as acute or chronic—depending on the healing time. Those classified as acute wounds heal uneventfully (with little or no complications) in the anticipated or predicted amount of time. Chronic wounds do not heal in the standard time frame and may linger for weeks, months or even years. In some case there are relatively few complications, other than slow healing. However, in other cases, chronic wounds can lead to amputation, non-ambulatory life styles, and/or death. Examples of chronic wounds include venous leg ulcers, arterial leg ulcers and neuropathic or diabetic ulcers and those caused by mechanical injury such as pressure ulcers. Usually, chronic wounds occur in an individual with an underlying pathology that prevents normal wound healing, such as co-morbidities of diabetes, heart disease, cancer, AIDS—just to name a few.

Open/Closed:

Wounds can be classified as open or closed. Open wounds are wounds with exposed underlying tissue and/or organs that are open to the outside environment (e.g., penetrating wounds). Closed wounds have damage that occurs without exposing the underlying tissue and organs (e.g., non-penetrating wounds).

Clean/Contaminated:

Another way to classify wounds is to determine if the wound is clean or contaminated. Clean wounds have no foreign materials or debris inside, whereas contaminated wounds or infected wounds might have dirt, fragments of the causative agent, bacteria or other foreign materials.

Wound Origin:

Wound origin can be either internal or external. Internal wounds typically result from impaired immune and nervous system functions and/or decreased supply of blood, oxygen or nutrients to that area; such as in cases of chronic medical illness (diabetes, atherosclerosis, deep vein thrombosis, etcetera). External wounds are usually caused by penetrating objects or non-penetrating trauma, and other miscellaneous causes discussed below.

Non-Penetrating Wounds:

These are usually the result of blunt trauma or friction with other surfaces; the wound does not break through the skin, and may include: abrasions (e.g., scraping of the outer skin layer), lacerations (e.g., a tear-like wound), contusions (e.g., swollen bruises due to accumulation of blood and dead cells under skin), and concussions (e.g., damage to the underlying organs and tissue on head with no significant external wound).

Penetrating Wounds:

These result from trauma that breaks through the full thickness of skin; reaching down to the underlying tissue and organs, and include: stab wounds (e.g., trauma from sharp objects, such as knives), skin cuts, surgical wounds (e.g., intentional cuts in the skin to perform surgical procedures), gunshot wounds (e.g., wounds resulting from firearms) and miscellaneous wounds, including thermal wounds from extreme temperatures, either hot or cold, (e.g., burns, sunburns and frostbite), chemical wounds (e.g., from contact with or inhalation of chemical materials that cause skin or lung damage, bites and stings (e.g., from humans, dogs, bats, rodents, snakes, scorpions, spiders and tick, and electrical wounds (These usually present with superficial burn-like or sting-like wounds secondary to the passage of high-voltage electrical currents through the body, and may include more severe internal damage).

Lower Extremity Wounds:

Lower extremity wounds are generally divided into arterial ulcers, venous ulcers, and neuropathic/diabetic wounds.

Arterial Leg Ulcers:

Arterial ulcers are also called ischemic ulcers. They are the result of tissue ischemia due to arterial insufficiency. These ulcers account for 5 percent to 20 percent of all leg ulcers, and they occur at the distal (remote) end of the arterial system. They are often seen on the tips of the toes. When arterial blood flow is interrupted by an obstruction or narrowing of an artery, it causes arterial insufficiency, which can lead to arterial ulcers. Another cause of occlusion is atherosclerosis.

Venous Leg Ulcers:

Any ulcer caused by stagnation of blood due to venous congestion or venous hypertension is known as a venous leg ulcer. Venous ulcers typically require both an optimal moist wound healing environment and edema-control measures, typically with compression. The limb must have sufficient arterial flow and be free from acute cellulitis or uncontrolled congestive heart failure. Therefore, determining perfusion is a key factor prior to applying any compression. Applying compression inappropriately can cause significant negative outcomes. A venous leg ulcer is usually located mid-calf to the heel, is medial or lateral, and can be circumferential. A venous leg ulcer is also usually poorly defined and often has jagged edges. The wound bed has ruddy red granulation tissue that is usually superficial and includes the presence of yellow fibrin. The drainage is moderate to heavy, and edema is usually generalized to the lower extremity. The pulse may be difficult to assess secondary to the edema. The wound may be moderately painful, which will often improve with a decrease in edema. Venous ulcers can occur in patients with superficial or perforator vein disease in addition to patients with deep vein disease. These wounds are most common in older adults; however, they account for 70 to 90 percent of all leg ulcers.

Neuropathic/Diabetic:

Neuropathy is a nerve disorder that results in lost or impaired function in the tissues of the affected nerve fibers. It is often associated with diabetes. Neuropathic/diabetic wounds result from damage to the autonomic, sensory or motor nerves and have an arterial perfusion deficit. They can be anywhere on the lower extremity, usually located on the foot, and are called diabetic foot ulcers.

Lymphedema:

Lymphedema is one of the most under-diagnosed and under-treated conditions affecting wound healing. There is no known cure, but like many chronic diseases, it can be managed successfully by patients if they are knowledgeable of the disease and its treatment. It is estimated that up to 250 million patients worldwide currently suffer with lymphedema.

The functioning lymphatic system is comprised of lymphatic vessels filled with lymphatic fluid, lymph nodes and organs. The lymphatics are really the "back up" system to remove fluid from the interstitial tissue when the venous system is overwhelmed. The lymphatic vessels closely mirror the vascular system. Its structure is similar to the venous system, consisting of one-way intraluminal valves to prevent reflux of lymph fluid.

Stages of Lymphedema:

Stage 0:

This stage is subclinical. Impaired lymph flow exists without clinical signs.

Stage I:

Soft edema that usually resolves on its own. The patient often reports that their legs are "puffy" after being upright for several hours, but the symptom disappears when they lie down.

Stage II:

Pitting, brawny edema. The skin tissue is firm and no longer soft, but not yet fibrotic.

Stage III:

Skin texture changes and displays "peau d' orange." This type of skin has the look and texture of an orange peel with prominent, indented pores. The epidermis forms thick scaly areas with cracks or deposits that may eventually develop a fibrotic warty-like tissue. Cracks and deep creases harbor bacteria and predispose the patient to infection.

Patients in lymphedema Stage II and III often have repeated episodes of cellulitis, as the lymph system is unable to clear bacteria from the interstitium to the lymph nodes and spleen for their destruction. Often, the clinical hallmark of undiagnosed lymphedema is numerous bouts of infection or non-healing wounds in the affected area. Interstitial fluid accumulation impairs wound healing by pressing on the vascular system, cutting off the delivery of oxygenation and nutrients. Local ischemia and resulting cellular waste products cannot be removed. Should the area develop weepy drainage, known as lymphorrhea, the proteins become irritating to the epidermis and subsequently contribute to a secondary infection. Other sequela associated with lymphedema includes complex regional pain syndrome, decreased sensation, limited range of motion and deconditioning.

It will be understood that regardless of it ordinary meaning the term "wounded area" will be defined herein as an area having an open and/or closed injury as well as any surrounding periphery that may, but not necessarily, involve a laceration or breaking of a membrane (e.g., skin) and may, but not necessarily, involve damage to underlying tissue. Indeed, in accordance with the present invention, many times a wound healing composition is associated with and/or applied to the surrounding periphery of the wound without actually applying the same to the open, closed, and/or irritated portion of the wound.

In accordance with the present invention, novel and advanced formulations and therapies for treating a wound as disclosed herein, including a hard-to-heal wound, are disclosed which comprise, consist essentially of, and/or consist of the steps of topically administering a wound healing composition to a wounded area, wherein the wound healing composition comprises, consists essentially of, and/or consists of at least one of: (a) one or more medicaments characterized as calcium channel blockers or pharmaceutically acceptable salts or solvates thereof; (b) one or more medicaments characterized as alpha-adrenergic antagonists or pharmaceutically acceptable salts or solvates thereof; (c) one or more medicaments characterized as direct vasodilators or pharmaceutically acceptable salts or solvates thereof; and (d) one or more medicaments characterized as phosphodiesterase type five inhibitors or pharmaceutically acceptable salts or solvates thereof; and (e) a hemorrheologic agent or pharmaceutically acceptable salts or solvates thereof; (f) a dermal penetrating agent or pharmaceutically acceptable salts or solvates thereof: and (g) a topical stimulating agent or pharmaceutically acceptable salts or solvates thereof.

In accordance with the present invention, the medicament characterized as a calcium channel blocker comprises, for example, dihydropyridines, phenylalkylamines, and benzothiazepines—just to name a few.

Non-limiting examples of dihydropyridines include amlodipine (Norvasc), aranidipine (Sapresta), azelnidipine (Calblock), barnidipine (HypoCa), benidipine (Coniel), cilnidipine (Atelec, Cinalong, Siscard), clevidipine (Cleviprex), isradipine (DynaCirc, Prescal), efonidipine (Landel), felodipine (Plendil), lacidipine (Motens, Lacipil), lercanidipine (Zanidip), manidipine (Calslot, Madipine), nicardipine (Cardene, Carden SR), nifedipine (Procardia, Adalat), nilvadipine (Nivadil), nimodipine (Nimotop) nisoldipine (Baymycard, Sular, Syscor), nitrendipine (Cardif, Nitrepin, Baylotensin), and pranidipine (Acalas).

Non-limiting examples of phenylalkylamines include verapamil (Calan, Isoptin), gallopamil, and fendiline.

Non-limiting examples of benzothiazepines include diltiazem (Cardizem).

It will be understood that the above-identified calcium channel blockers are readily available for any one of a number of common commercial sources.

In one aspect of the present invention, the medicament characterized as a calcium channel blocker is preferably represented by the following chemical structure:

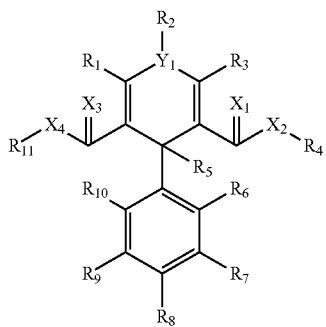

wherein $R_{1-11}$ are the same or different and comprise H, a hydroxy group, a primary, secondary, or tertiary amine, a halide, $NO_2$, $SO_3H$, $CN$, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof, preferably with the proviso that at least one of $R_6$-$R_{10}$ comprises a halide, $NO_2$, $SO_3H$, or $CN$; wherein $X_{1-4}$ are the same or different and comprise oxygen, sulfur, or selenium; and wherein $Y_1$ comprises nitrogen or phosphorus. Preferably, the medicament characterized as a calcium channel blocker is represented by the following chemical structure:

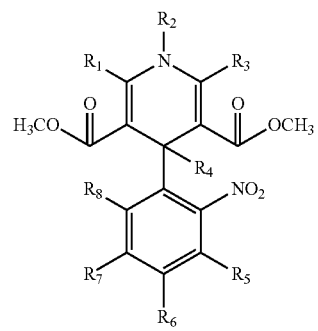

wherein $R_{1-8}$ are the same or different and comprise H, a hydroxy group, a primary, secondary, or tertiary amine, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof. By way of a non-limiting specific example, the medicament characterized as a calcium channel blocker may comprise the following chemical structure:

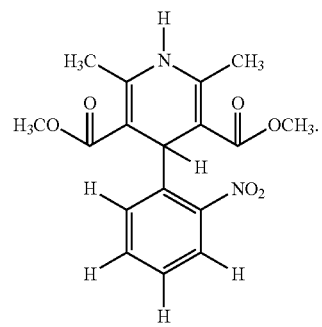 [SMILES: COC(=O)C1=C(C)NC(C)=C(C(=O)OC)C1c1ccccc1[N+](=O)[O-]]

For purposes of clarity, and in an attempt to eliminate any potential ambiguity associated with the nomenclature of the above-identified medicament, it will be understood that a specific medicament provided herein above is defined as 3,5-pyridinedicarboxylic acid, 1,4-dihydro-2,6-dimethyl-4-(2-nitrophenyl)-dimethyl ester which is commercially available from Bayer Pharmaceuticals Corporation.

It will be understood that an "effective amount" of the medicament characterized as a calcium channel blocker is an amount that facilitates healing of a wound, and can be administered, via any one of a number of conventional means, to a patient/subject. Preferably, the effective dose ranges in concentration from approximately 0.5% (wt.) to approximately 40% (wt.) approximately q.d.-q.i.d., and more preferably ranges in concentration from approximately 2% (wt.) to approximately 15% (wt.) approximately q.d.-q.i.d. However, the effective amount will vary depending upon many factors including, for example, the size and type of wound being treated.

In accordance with the present invention, the medicament characterized as an alpha-adrenergic antagonist, includes, for example, non-selective α-adrenergic blockers, such as phenoxybenzamine, phentolamine, tolazoline, and trazodone, selective $\alpha_1$-adrenergic blockers, such as alfuzosin (Uroxatral, Xatral—available from Sanofi Aventis), doxazosin (Cardura, Carduran—available from Pfizer), prazosin (Minipress, Vasoflex, Hypovase), silodosin, tamsulosin (Flomaxtra, Urimax, Flomax—available from Astellas Pharma) and terazosin (Hytrin), and selective $\alpha_2$-adrenergic blockers, such as Atipamezole, Idazoxan, Mirtazapine, and Yohimbine—just to name a few. It will be understood that many of the above-identified alpha-adrenergic antagonists are readily available for any one of a number of common commercial sources.

In one aspect of the present invention, the medicament characterized as an alpha-adrenergic antagonist is preferably represented by one or more of the following chemical structures:

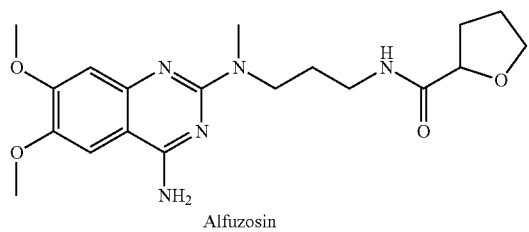

Alfuzosin
N-(3-((4-amino-6,7-dimethoxyquinazolin-2-yl)(methyl)amino)
propyl)tetrahydrofuran-2-carboxamide

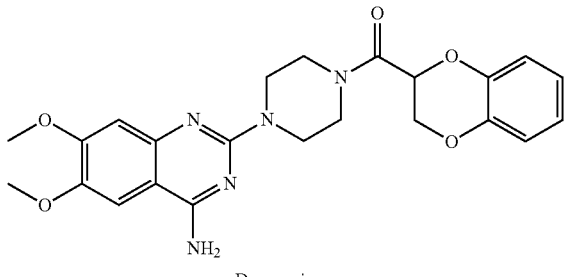

Doxazosin
(4-(4-amino-6,7-dimethoxyquinazolin-2-yl)piperazin-1-yl)
(2,3-dihydrobenzo[b][1,4]dioxin-2-yl)methanone lp;1p

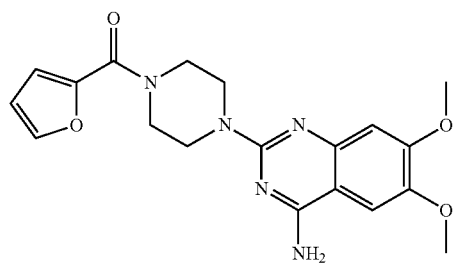

Prazosin
(4-(4-amino-6,7-dimethoxyquinazolin-2-yl)piperazin-1-yl)
(furan-2-yl)methanone

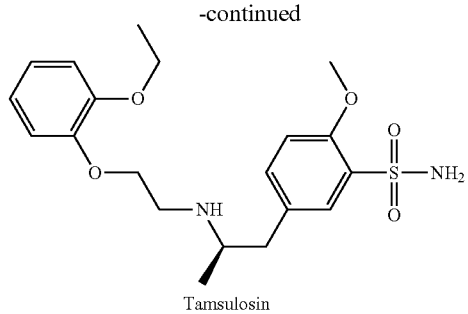

Tamsulosin
(R)-5-(2-(2-(2-ethoxyphenoxyl)ethylamino)propyl)-
2-methoxybenzenesulfonamide

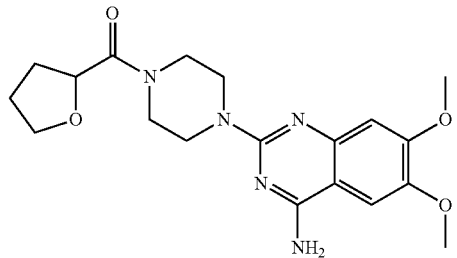

Terazosin
(4-(4-amino-6,7-dimethoxyquinazolin-2-yl)piperazin-1-yl)
(tetrahydrofuran-2-yl)methanone and pharmaceutically acceptable salts thereof.

It will be understood that an "effective amount" of the medicament characterized as an alpha-adrenergic antagonist is an amount that facilitates healing of a wound, and can be administered, via any one of a number of conventional means, to a patient/subject. Preferably, the effective dose ranges in concentration from approximately 0.5% (wt.) to approximately 40% (wt.) approximately q.d.-q.i.d., and more preferably ranges in concentration from approximately 2% (wt.) to approximately 15% (wt.) approximately q.d.-q.i.d. However, the effective amount will vary depending upon many factors including, for example, the size and type of wound being treated.

In accordance with the present invention, the medicament characterized as a direct vasodilator, includes, for example, minoxidil (Rogaine, Regaine), hydralazine (Apresoline), isoxsuprine, and papaverine—just to name a few. It will be understood that many of the above-identified direct vasodilators are readily available for any one of a number of common commercial sources.

In one aspect of the present invention, the medicament characterized as a direct vasodilator is preferably represented by one or more of the following chemical structures:

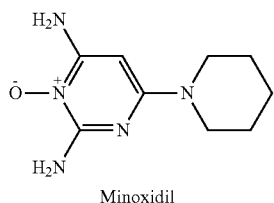

Minoxidil
2,6-diamino-4-(piperidin-1-yl)
pyrimidine
1-oxide

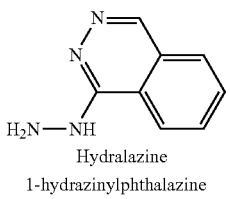

Hydralazine
1-hydrazinylphthalazine

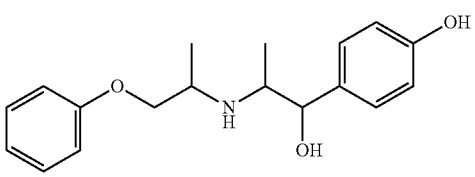

Isoxsuprine
4-(1-hydroxy-2-(1-phenoxypropan-2-ylamino)propyl)phenol

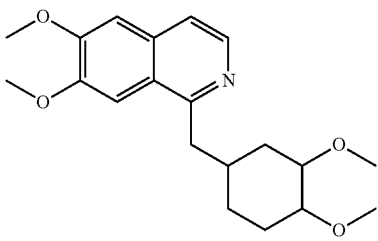

Papaverine
1-((3,4-dimethoxycyclohexyl)methyl)-6,7-dimethoxyisoquinoline and pharmaceutically acceptable salts thereof.

It will be understood that an "effective amount" of the medicament characterized as a direct vasodilator is an amount that facilitates healing of a wound, and can be administered, via any one of a number of conventional means, to a patient/subject. Preferably, the effective dose ranges in concentration from approximately 0.5% (wt.) to approximately 40% (wt.) approximately q.d.-q.i.d., and more preferably ranges in concentration from approximately 2% (wt.) to approximately 15% (wt.) approximately q.d.-q.i.d. However, the effective amount will vary depending upon many factors including, for example, the size and type of wound being treated.

In accordance with the present invention, the medicament characterized as a phosphodiesterase type five inhibitors, includes, for example, sildenafil (Viagra, Revatio—available from Pfizer), tadalafil (Clalis—available from Lilly ICOS), Vardenafil (Levitra—Bayer AG)—just to name a few. It will be understood that many of the above-identified phosphodiesterase type five inhibitors are readily available for any one of a number of common commercial sources.

In one aspect of the present invention, the medicament characterized as a phosphodiesterase type five inhibitor is preferably represented by one or more of the following chemical structures:

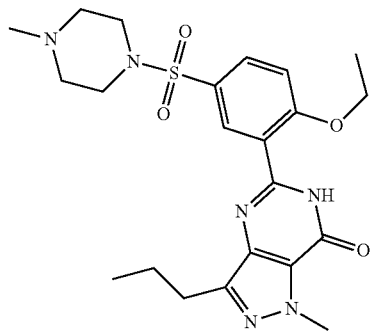

Sildenafil
5-(2-ethoxy-5-(4-methylpiperazin-1-ylsulfonyl)phenyl)-1-methyl-3-propyl-1H-pyrazolo[4,3-d]pyrimidin-7(6H)-one

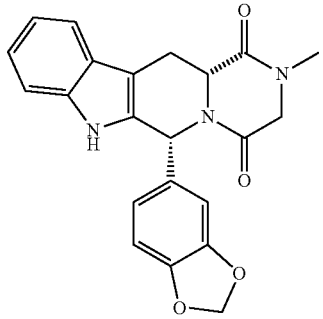

Tadalafil
(6R-trans)-6-(1,3-benzodioxol-5-yl)-2,3,6,7,12,12a-hexahydro-2-methyl-pyrazino[1',2':1,6] pyrido[3,4-b]indole-1,4-dione

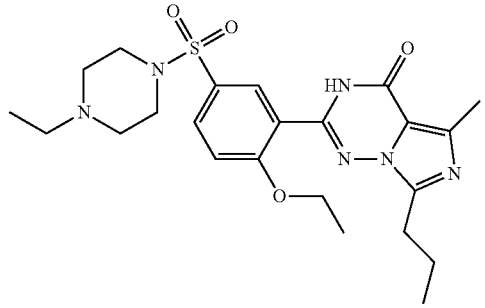

Vardenafil
2-(2-ethoxy-5-(4-ethylpiperazin-1-ylsulfonyl)phenyl)-5-methyl-7-propylimidazo[1,5-f][1,2,4]triazin-4(3H)-one and pharmaceutically acceptable salts thereof.

It will be understood that an "effective amount" of the medicament characterized as a phosphodiesterase type five inhibitor is an amount that facilitates healing of a wound, and can be administered, via any one of a number of conventional means, to a patient/subject. Preferably, the effective dose ranges in concentration from approximately 0.5% (wt.) to approximately 40% (wt.) approximately q.d.-q.i.d., and more preferably ranges in concentration from approximately 2% (wt.) to approximately 15% (wt.) approximately q.d.-q.i.d. However, the effective amount will vary depending upon many factors including, for example, the size and type of wound being treated.

For purposes of the present disclosure, the second medicament (characterized as a hemorrheologic agent) is preferably represented by the following chemical structure:

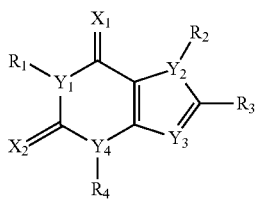

wherein $R_{1-4}$ are the same or different and comprise H, a hydroxy group, a primary, secondary, or tertiary amine, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof; wherein $X_{1-2}$ are the same or different and comprise oxygen, sulfur, or selenium; and wherein $Y_{1-4}$ are the same or different and comprise nitrogen or phosphorus. Preferably, the second medicament is represented by the following chemical structure:

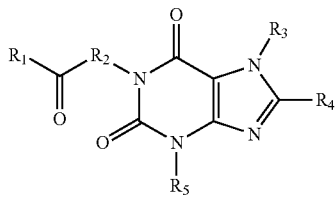

wherein $R_{1-5}$ are the same or different and comprise H, a hydroxy group, a primary, secondary, or tertiary amine, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof. One specific example includes the following chemical structure:

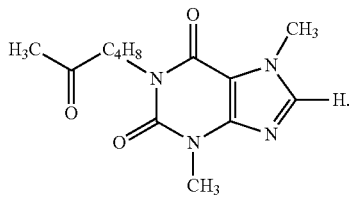

For purposes of clarity, and in an attempt to eliminate any potential ambiguity associated with the nomenclature of the above-identified second medicament, it will be understood that a specific medicament provided herein above is defined as 1-(5-oxohexyl)-3,7-dimethylxanthine, which is commercially available from Aventis Pharmaceuticals.

It will be understood that an "effective amount" of the above-identified second medicaments is an amount that facilitates healing of a wound, and can be administered, via any one of a number of conventional means, to a patient/subject. Preferably, the effective dose ranges in concentration from approximately 0.5% (wt.) to approximately 40% (wt.) approximately q.d.-q.i.d., and more preferably ranges in concentration from approximately 5% (wt.) to approximately 15% (wt.) approximately q.d.-q.i.d. However, the effective amount will vary depending upon many factors including, once again for example, the size and type of wound being treated.

In accordance with the present invention, the dermal penetrating agent is preferably represented by the following chemical structure:

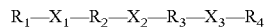

$$R_1-X_1-R_2-X_2-R_3-X_3-R_4$$

wherein $R_{1-4}$ are the same or different and comprise H, a hydroxy group, a primary, secondary, or tertiary amine, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof; and wherein $X_{1-3}$ are the same or different and comprise oxygen, sulfur, or selenium. Preferably, the dermal penetrating agent is represented by the following chemical structure:

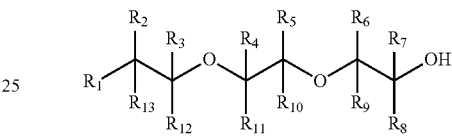

wherein $R_{1-13}$ are the same or different and comprise H, a hydroxy group, a primary, secondary, or tertiary amine, a straight or branched alkyl, cycloalkyl, polycycloalkyl, heterocycloalkyl, aryl, alkaryl, aralkyl, alkoxy, alkenyl, alkynyl, or carbonyl group containing approximately 1 to approximately 50 carbon atom(s), a silyl or siloxyl group containing approximately 1 to approximately 50 silicon atom(s), and combinations thereof. A specific example includes the following chemical structure:

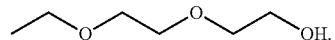

For purposes of clarity, and in an attempt to eliminate any potential ambiguity associated with the nomenclature of the above-identified dermal penetrating agents, it will be understood that a specific dermal penetrating agent provided herein above is defined as 2-(2-ethoxy-ethoxy)-ethanol, which is commercially available from Pfaltz and Bauer.

It will be understood that an "effective amount" of the above-identified dermal penetrating agent is an amount that facilitates healing of a wound, and can be administered, via any one of a number of conventional means, to a patient/subject. Preferably, the effective dose ranges in concentration from approximately 0.5% (wt.) to approximately 60% (wt.) approximately q.d.-q.i.d., and more preferably ranges in concentration from approximately 5% (wt.) to approximately 20% (wt.) approximately q.d.-q.i.d. However, the effective amount will vary depending upon many factors including, as mentioned herein, the size and type of wound being treated In another aspect of the present invention, the formulation includes a topical stimulating agent. In this embodiment the topical stimulating agent preferably comprises, for example, a non-alkylated silicone copolyol, such as DC5329 (PEG-12 dimethicone, o/w emulsification, HLB=12) which is commercially available from Dow Corning, and/or an alkylated silicone copolyol, such as ABIL EM 90 (cetyl PEG/PPG- 10/1 dimethicone, w/o emulsification, HLB=5) which is commercially available from Goldschmidt, and/or DC 5200 (lauryl PEG/PPG-18/8 methicone, w/o emulsification, HLB=4) which is commercially available from Dow Corning.

Preferably, the topical stimulating agent comprises both a non-alkylated silicone copolyol and an alkylated silicone copolyol, such that their composite HLB ranges from approximately 9 to approximately 12, more preferably from approximately 9.5 to approximately 11.5, and yet more preferably from approximately 10 to approximately 11. It will be understood that the composite HLB is calculated using the weighted average of the topical stimulating agents. Without being bound by any particular theory, it is believed that utilization of a mixture of a non-alkylated silicone copolyol with an alkylated silicone copolyol presenting a composite HLB facilitates topical stimulation via HLB compatibility with the wounded area. In one embodiment, the advanced formulations and therapies that utilize the topical stimulating agents disclosed herein form stable dispersions and/or emulsions.

It will be understood that an "effective amount" of the above-identified topical stimulating agent or mixtures thereof is an amount that facilitates healing of a wound, and can be administered, via any one of a number of conventional means, to a patient/subject. Preferably, the effective dose ranges in concentration from approximately 0.25% (wt.) to approximately 60% (wt.) approximately q.d.-q.i.d., and more preferably ranges in concentration from approximately 5% (wt.) to approximately 20% (wt.) approximately q.d.-q.i.d. However, the effective amount will vary depending upon many factors including, as mentioned herein, the size and type of wound being treated.

Example 1

In support of the present invention, several experiments were conducted to evaluate the efficacy of above-identified medicaments in treating conventionally non-healing wounds. A topical formulation (80 mg/ml) was prepared comprising approximately 8% (wt.) of nifedipine (i.e. 3,5-pyridinedicarboxylic acid, 1,4-dihydro-2,6-dimethyl-4-(2-nitrophenyl)-dimethyl ester), 10% (wt.) pentoxifylline (i.e. 1-(5-oxohexyl)-3,7-dimethylxanthine), 12.5% (wt.) ethoxy diglycol (i.e. 2-(2-ethoxy-ethoxy)-ethanol), 22% (wt.) lecithin/isopropyl palmitate, and Pluronic F-127 (generically known as poloxamer 407. CAS-No. 9003-11-6, propoxylated polyethylene glycol) (to 100%). The above-identified composition was topically administered to the outer periphery of a plurality of subjects having a wounded area approximately q.d.-q.i.d., wherein it was verified that wounds which ordinarily were difficult or impossible to heal were, indeed, healed—and in some cases prevented amputation.

In accordance with the present invention, other transdermal bases suitable for use comprise Krisgel, Pluronic Lecithin Organogel, Lipoderm (PCCA), Anhydrous Lipoderm (PCCA), Lipoderm HMW (PCCA), Lipoderm ActiveMax (PCCA), Versapro (Medisca), PLO Mediflo (Medisca), Hydrogel (Medisca), Transdermal Pain Base (Medisca), PLO Transdermal (Medisca), Meriderm (Medisca) Liposome Cream (Letco), and Medium Cream (Letco).

Additional formularies are provided in Examples 2-43 below.

Example 2

| Medicament/Ingredient | Amount (Wt. %) |
|---|---|
| nifedipine | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 3

| Medicament/Ingredient | Amount (Wt. %) |
|---|---|
| alfuzosin | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 4

| Medicament/Ingredient | Amount (Wt. %) |
|---|---|
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 5

| Medicament/Ingredient | Amount (Wt. %) |
|---|---|
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 6

| Medicament/Ingredient | Amount (Wt. %) |
|---|---|
| nifedipine | 2-15% |
| alfuzosin | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 7

| Medicament/Ingredient | Amount (Wt. %) |
|---|---|
| nifedipine | 2-15% |
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 8

| Medicament/Ingredient | Amount (Wt. %) |
|---|---|
| nifedipine | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 9

| Medicament/Ingredient | Amount (Wt. %) |
|---|---|
| alfuzosin | 2-15% |
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 10

| Medicament/Ingredient | Amount (Wt. %) |
|---|---|
| Alfuzosin | 2-15% |
| Sildenafil | 2-15% |
| Pentoxifylline | 5-15% |
| ethoxy diglycol | 15-30% |
| lecithin:isopropyl palmitate | 2-20% |
| Pluronic F-127 20% gel | qs 100% |

Example 11

| Medicament/Ingredient | Amount (Wt. %) |
|---|---|
| minoxidil | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 12

| Medicament/Ingredient | Amount (Wt. %) |
|---|---|
| nifedipine | 2-15% |
| alfuzosin | 2-15% |
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 13

| Medicament/Ingredient | Amount (Wt. %) |
|---|---|
| nifedipine | 2-15% |
| alfuzosin | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 14

| Medicament/Ingredient | Amount (Wt. %) |
|---|---|
| alfuzosin | 2-15% |
| minoxidil | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 15

| Medicament/Ingredient | Amount (Wt. %) |
|---|---|
| nifedipine | 2-15% |
| minoxidil | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 16

| Medicament/Ingredient | Amount (Wt. %) |
|---|---|
| nifedipine | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 17

| Medicament/Ingredient | Amount (Wt. %) |
|---|---|
| alfuzosin | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 18

| Medicament/Ingredient | Amount (Wt. %) |
|---|---|
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 19

| Medicament/Ingredient | Amount (Wt. %) |
|---|---|
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 20

| Medicament/Ingredient | Amount (Wt. %) |
|---|---|
| nifedipine | 2-15% |
| alfuzosin | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 21

| Medicament/Ingredient | Amount (Wt. %) |
|---|---|
| nifedipine | 2-15% |
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 22

| Medicament/Ingredient | Amount (Wt. %) |
|---|---|
| nifedipine | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 23

| Medicament/Ingredient | Amount (Wt. %) |
|---|---|
| alfuzosin | 2-15% |
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 24

| Medicament/Ingredient | Amount (Wt. %) |
|---|---|
| alfuzosin | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 25

| Medicament/Ingredient | Amount (Wt. %) |
|---|---|
| minoxidil | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 26

| Medicament/Ingredient | Amount (Wt. %) |
|---|---|
| nifedipine | 2-15% |
| alfuzosin | 2-15% |
| minoxidil | 2-15% |
| pentoxifylline | 5-15% |
| ethoxy diglycol | 15-30% |
| lecithin:isopropyl palmitate | 2-20% |

-continued

| Medicament/Ingredient | Amount (Wt. %) |
| --- | --- |
| Pluronic F-127 20% gel | qs 100% |
| alkylated/non-alkyl silicone copolyol | 0.5-15% |

Example 27

| Medicament/Ingredient | Amount (Wt. %) |
| --- | --- |
| nifedipine | 2-15% |
| alfuzosin | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 28

| Medicament/Ingredient | Amount (Wt. %) |
| --- | --- |
| alfuzosin | 2-15% |
| minoxidil | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 29

| Medicament/Ingredient | Amount (Wt. %) |
| --- | --- |
| nifedipine | 2-15% |
| minoxidil | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol | 0.5-15% |

Example 30

| Medicament/Ingredient | Amount (Wt. %) |
| --- | --- |
| nifedipine | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 31

| Medicament/Ingredient | Amount (Wt. %) |
| --- | --- |
| alfuzosin | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 32

| Medicament/Ingredient | Amount (Wt. %) |
| --- | --- |
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 33

| Medicament/Ingredient | Amount (Wt. %) |
| --- | --- |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 34

| Medicament/Ingredient | Amount (Wt. %) |
| --- | --- |
| nifedipine | 2-15% |
| alfuzosin | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 35

| Medicament/Ingredient | Amount (Wt. %) |
| --- | --- |
| nifedipine | 2-15% |
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |

Example 36

| Medicament/Ingredient | Amount (Wt. %) |
|---|---|
| alkylated/non-alkyl silicone copolyol with composite HLB 9-12 | 0.5-15% |

Example 36

| Medicament/Ingredient | Amount (Wt. %) |
|---|---|
| nifedipine | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 37

| Medicament/Ingredient | Amount (Wt. %) |
|---|---|
| alfuzosin | 2-15% |
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 38

| Medicament/Ingredient | Amount (Wt. %) |
|---|---|
| alfuzosin | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 39

| Medicament/Ingredient | Amount (Wt. %) |
|---|---|
| minoxidil | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 40

| Medicament/Ingredient | Amount (Wt. %) |
|---|---|
| nifedipine | 2-15% |
| alfuzosin | 2-15% |
| minoxidil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 41

| Medicament/Ingredient | Amount (Wt. %) |
|---|---|
| nifedipine | 2-15% |
| alfuzosin | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 42

| Medicament/Ingredient | Amount (Wt. %) |
|---|---|
| alfuzosin | 2-15% |
| minoxidil | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

Example 43

| Medicament/Ingredient | Amount (Wt. %) |
|---|---|
| nifedipine | 2-15% |
| minoxidil | 2-15% |
| sildenafil | 2-15% |
| pentoxifylline | 5-15% |
| ethoxy diglycol | 15-30% |
| lecithin:isopropyl palmitate | 2-20% |
| Pluronic F-127 20% gel | qs 100% |
| alkylated/non-alkyl silicone copolyol with composite HLB 9-12 | 0.5-15% |

In support of the present invention, several studies were conducted to evaluate the efficacy of the advanced formulations and associated therapies for treating hard-to-heal wounds.

Case 1

Figure 2:
FIG. 2 of the drawings is a post-therapy photograph of a wound of patient one.

Patient one was a 77 year-old Caucasian female with a diagnosis of a chronic heel ulceration on her right foot that has persisted for more than one year. Patient one has already undergone a below the knee amputation of the left lower extremity and wears a prosthesis on the same. Patient one presented co-morbidities including age, venous stasis, chronic lymphedema, morbid obesity, cardiac history, diabetes, and peripheral vascular disease. Patient one also presented visual acuity problems, diabetic neuropathy and was diagnosed with cellulitis, an infected right foot, and osteomyelitis. At the time of initial consultation, patient one was also being treated with steroids for gout and further presented pre-renal failure. Patent one received four other professional consultations that resulted in a recommendation for a below the knee amputation of the right lower extremity. If such a recommendation was followed, patient one would have committed to a wheelchair for life. FIG. 1 is a photograph of Patient one's heel wound observed during the initial consultation. Patient one was treated with a novel wound healing formulation of the present invention. In addition to topical application of the advanced formulation, the therapy protocol for patient one included whirlpool and wound vacuum therapy. Remarkably, and without subsequent surgery, Patient one's wound healed in approximately 307 days (See FIG. 2). Notably, if untreated, patient one, would likely have been afflicted with chronic infection, septicemia, renal failure, amputation, dialysis, and possible death. With conventional treatment patient one would have been bedridden or wheelchair dependent—at best.

Case 2

Figure 3:
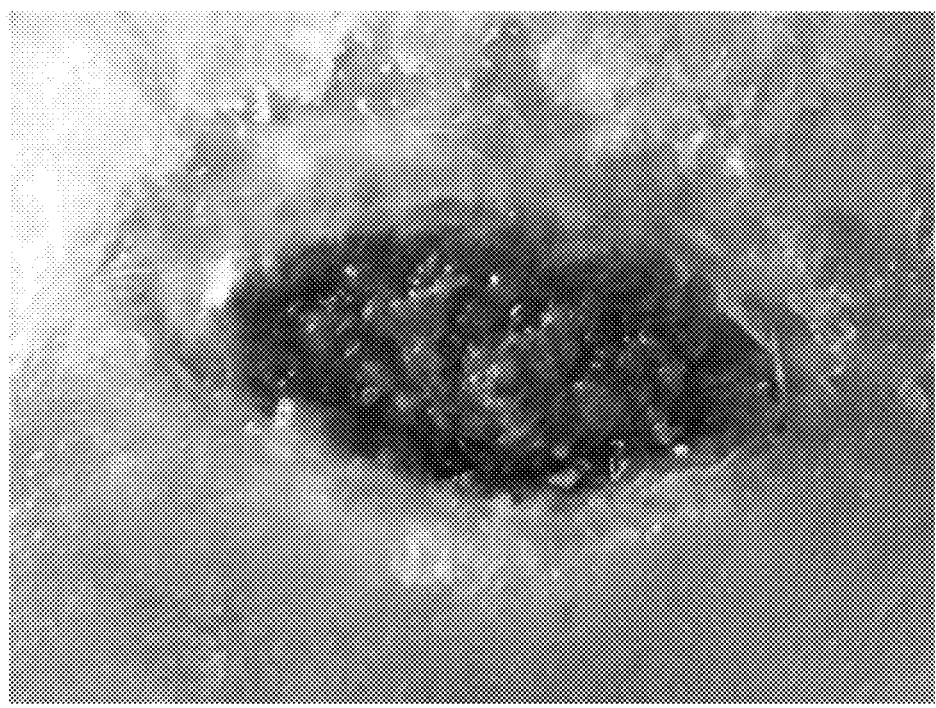
FIG. 3 of the drawings is a pre-therapy photograph of a wound of patient two.
Figure 4:
FIG. 4 of the drawings is a post-therapy photograph of a wound of patient two.

Patient two was a 75 year-old Caucasian female with a history of chronic venous stasis lymphedema over the medial side of left foot, which had recently has had a split thickness skin graft at another institution to cover the defect. The patient was non compliant about wearing compression stockings and with the increased swelling, lymphedema, venous stasis and diabetes did not want the wound touched. The edema had separated the non-pliable graft from the swelling skin and separated the wound (See FIG. 3). Patient two was treated with a novel wound healing formulation of the present invention. As is shown in FIG. 4, patient two's wound had significantly reduced in size with epithilization nearly complete. At the time of photograph in FIG. 4 was taken, patient two was discharged to move south with her daughter.

Case 3

Figure 5:
FIG. 5 of the drawings is a pre-therapy photograph of a wound of patient three.
Figure 6:
FIG. 6 of the drawings is a post-therapy photograph of a wound of patient three.

Patient three was a 78 year-old Caucasian female with a diagnosis of a chronic contaminated draining wound for greater than ten years. Patient three presented co-morbidities including age, venous stasis, chronic lymphedema, morbid obesity, cardiac history, diabetes, and peripheral vascular disease. Patient three further presented chronic cellulitis, hemosiderin staining and was chronically treated with antibiotic therapy. Patient three also presented pre-renal failure via BUN and Creatinine levels. FIG. 5 is a photograph of Patient three's wound during the initial consultation. Patient three was treated with a novel wound healing formulation of the present invention along with whirlpool and wound vacuum therapy. Remarkably, the wound treated for 10 years without resolution healed in three months without pain, antibiotics, or surgery (See FIG. 6). Notably, if untreated, patient three, would likely have been afflicted with continued chronic weeping, pain, edema, cellulitis, hospitalization, and antibiotic use could have led to renal failure. Moreover, extremely long-term chronic wounds can convert to skin cancers, basal and squamous cell which can lead to radiation, dialysis, and amputation.

Case 4

Figure 7:
FIG. 7 of the drawings is a pre-therapy photograph of a wound of patient four.
Figure 8:
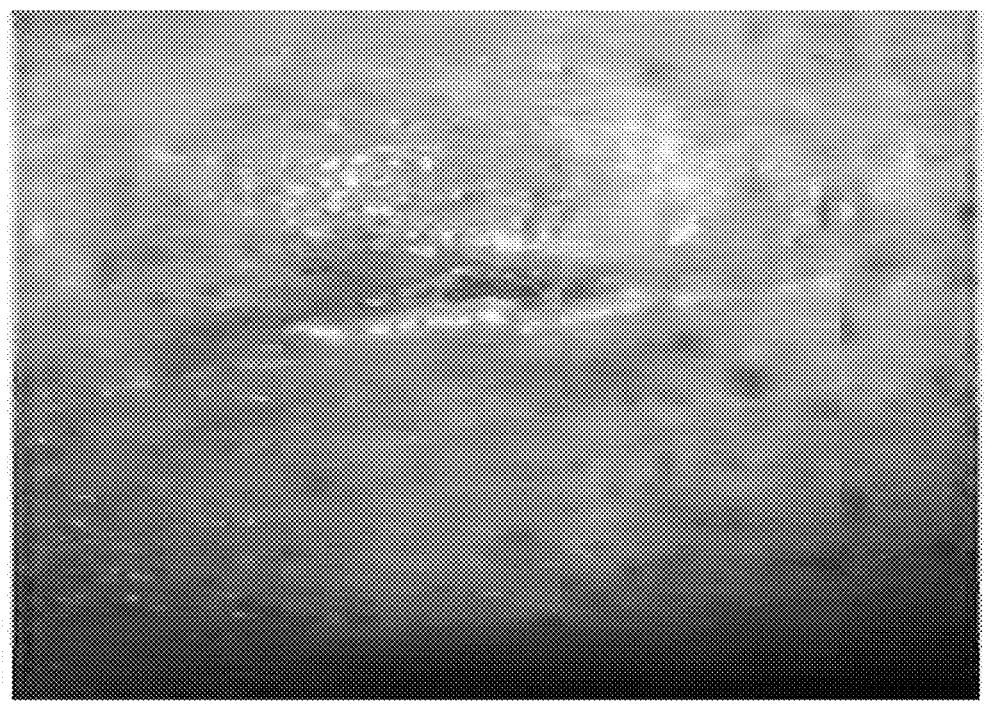
FIG. 8 of the drawings is a post-therapy photograph of a wound of patient four.

Patient four was a 63 year-old Caucasian male with a diagnosis of a work related trauma wound to the lower leg. Patient four presented co-morbidities including cardiac arrhythmia, obesity, diabetes, venous stasis, and chronic lymphedema. Patient four developed an infected hematoma with surrounding cellulitis, painful mass, swelling and the beginning of tissue loss. FIG. 7 is a photograph of Patient four's wound during postoperative consultation. Patient one was treated with a novel wound healing formulation of the present invention. Remarkably, wound epithelized in less than three weeks (See FIG. 8). Notably, if untreated, patient four, would have likely undergone amputation from the incident.

In accordance with the present invention, therapy or treatment protocols preferably include three components identified below. These are believed to yield a remarkable effect to a wound. These protocols are based upon the understanding that wounds, regardless of etiology, typically include a disruption of the vascular supply, and thus blood flow to the area. Therefore, the wounded area is preferably cleansed daily. This typically entails washing away of bacterial contamination and encrusted exudate of protein coming from the wound along with necrotic tissue and debris. From simple washing to whirlpools, whose agitating warm water debrides tissue and the warmth of water increases circulation to skin. This whirlpool action acts as a debridement mechanism as well to cleanse the wound. Other modalities include surgery (cutting away necrotic tissue) pulse lavage, enzymatic debridement, and bio-surgical technique (maggot therapy). Second, the pressure associated with the wound is preferably reduced. This preferably includes the internal and external pressure of the wound. As such, the common use of pressure dressings is contraindicated and/or eliminated. Positioning, elevation, compression garments, diuretics, and pneumatic compression devices are preferably used to reduce the hydrostatic pressure in an extremity. In addition, in some cases there is the use of pressure relief mattresses. Decreasing pressure on the elastic skin (subdermal plexus) reduces the narrowing of the vessels which are stretched to maximum capacity and decrease the diameter of the vessel. This decrease in pressure improves blood flow to and from the wound area. Lastly, an increase in the local circulation occurs by application of the medicaments and formulations disclosed herein. This is preferably delivered on the leading edge of the intact skin, where the cells reproduce, and where mitosis begins. Deformation of cell nuclei by pressure and lack of oxygen by edema causes the death of the progenitors of the skin. The local absorption of the transdermal medicament applied peripherally to the wound is believed to vasodilate the subdermal plexus—thus increasing blood flow and carrying the necessary oxygen to initiate the mitotic phase of cell reproduction and assists in the transmigration across the open wound to epithelialize and close the wound.

The foregoing description merely explains and illustrates the invention and the invention is not limited thereto except insofar as the appended claims are so limited, as those skilled in the art who have the disclosure before them will be able to make modifications without departing the scope of the invention.

What is claimed and desired to be secured by Letters Patent of the United States is:

1. A method for healing a wound, consisting of the steps of:
    topically administering a wound healing composition to a lymphedema wound, wherein the wound healing composition consists of:
        from 2% to 15% by weight of a medicament characterized as a calcium channel blocker or pharmaceutically acceptable salts or solvates thereof;
        from 5% to 15% by weight of a medicament characterized as a hemorrheologic agent or pharmaceutically acceptable salts or solvates thereof;
        from 15% to 30% by weight of a dermal penetrating agent or pharmaceutically acceptable salts or solvates thereof;
        from 2% to 20% by weight of lecithin isopropyl palmitate; and
        from 0.5% to 15% by weight of a topical stimulating agent or pharmaceutically acceptable salts or solvates thereof, wherein the topical stimulating agent consists of a mixture of a non-alkylated silicone copolyol and an alkylated silicone copolyol having a composite HLB ranging from 10 to 11, and wherein any remainder consists of a transdermal base.

2. A method for healing a wound, consisting of the steps of:
    topically administering a wound healing composition to a lymphedema wound, wherein the wound healing composition consists of:
        from 2% to 15% by weight of nifedipine;
        from 5% to 15% by weight of 1-(5-oxohexyl)-3,7-dimethylxanthine;
        from 15% to 30% by weight of 2-(2-ethoxy-ethoxy)-ethanol;
        from 2% to 15% by weight of alfuzosin;
        from 2% to 15% by weight of minoxidil;
        from 2% to 15% by weight of sildenafil;
        from 2% to 20% by weight of lecithin isopropyl palmitate; and
        from 0.5% to 15% by weight of a topical stimulating agent or pharmaceutically acceptable salts or solvates thereof, wherein the topical stimulating agent consists of a mixture of a non-alkylated silicone copolyol and an alkylated silicone copolyol having a composite HLB ranging from 10 to 11, and wherein any remainder consists of a transdermal base gel.

* * * * *